United States Patent [19]

Marsoner et al.

[11] Patent Number: 4,657,736
[45] Date of Patent: Apr. 14, 1987

[54] SENSOR ELEMENT FOR DETERMINING THE OXYGEN CONTENT AND A METHOD OF PREPARING THE SAME

[75] Inventors: Hermann Marsoner; Herbert Kroneis; Otto Wolfbeis, all of Graz, Austria

[73] Assignee: AVL AG, Schaffhausen, Switzerland

[21] Appl. No.: 883,430

[22] Filed: Jul. 14, 1986

Related U.S. Application Data

[63] Continuation of Ser. No. 553,385, Nov. 18, 1983, abandoned.

[30] Foreign Application Priority Data

Nov. 23, 1982 [AT] Austria .................................. 4265/82

[51] Int. Cl.$^4$ ........................ G01J 3/30; G01N 21/26; G01N 21/48; G01N 33/16
[52] U.S. Cl. ........................................ 422/56; 422/87; 436/172; 436/136; 524/588
[58] Field of Search .............................. 428/447, 690; 250/462.1; 252/408.1; 422/52, 55, 56, 87; 436/136, 138, 172

[56] References Cited

U.S. PATENT DOCUMENTS

| | | | |
|---|---|---|---|
| 2,907,882 | 10/1959 | Patten | 428/690 X |
| 3,612,866 | 10/1971 | Stevens | 422/56 X |
| 3,776,761 | 12/1973 | Kato et al. | 428/690 X |
| 3,881,869 | 5/1975 | Neti et al. | 436/172 X |
| 4,003,707 | 1/1977 | Lübbers et al. | 436/172 |
| 4,349,509 | 9/1982 | Yoshikawa et al. | 422/56 X |
| 4,409,277 | 10/1983 | Michel | 428/690 X |
| 4,526,752 | 7/1985 | Perlman et al. | 422/87 X |

FOREIGN PATENT DOCUMENTS

| | | | |
|---|---|---|---|
| 2557419 | 6/1976 | Fed. Rep. of Germany | 422/52 |
| 2508637 | 11/1979 | Fed. Rep. of Germany | . |
| 0099070 | 7/1980 | Japan | 436/136 |
| 575639 | 5/1976 | Switzerland | 250/462.1 |
| 0893853 | 12/1981 | U.S.S.R. | 436/136 |

*Primary Examiner*—Nancy Swisher
*Attorney, Agent, or Firm*—Watson, Cole, Grindle & Watson

[57] ABSTRACT

In an $O_2$ sensor element which contains a fluorescent indicator substance, a polymerized silicone polymer is used as a carrier material in which the indicator substance is incorporated in solubilized form and in an at least approximately homogeneous distribution. Solubilization of the indicator substance may essentially be performed in analogy to Friedel-Crafts alkylation of aromatics, which will increase solubility of the indicator substance in the polymer carrier without affecting quenching behavior.

18 Claims, 1 Drawing Figure

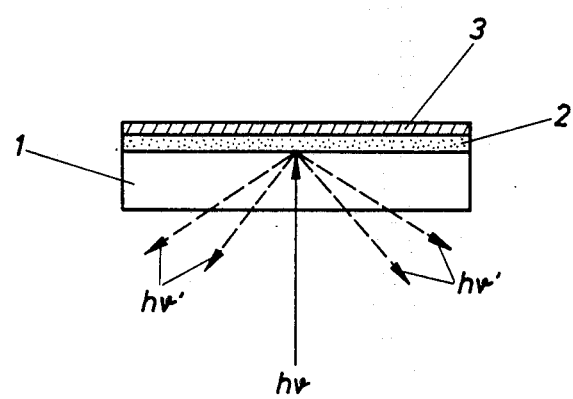

SENSOR ELEMENT FOR DETERMINING THE OXYGEN CONTENT AND A METHOD OF PREPARING THE SAME

This application is a continuation, of application Ser. No. 553,385, filed Nov. 18, 1983, now abandoned.

BACKGROUND OF THE INVENTION

This invention relates to a sensor element for determining the $O_2$ content of a sample, comprising an indicator substance fluorescing with the amount of $O_2$ acting upon it, which may be brought into contact with the sample to be measured at least partially and which will give off fluorescent light upon excitation, the indicator substance being incorporated in a polymer carrier matrix in an at least approximately homogeneous distribution, and to a method of preparing such a sensor element.

DESCRIPTION OF THE PRIOR ART

It is known that molecular oxygen will influence the intensity of fluorescence of a large number of organic substances, e.g., polycyclic aromatic hydrocarbons. In such cases the molecular oxygen will interact with the molecule activated by the excitation light, drawing energy from the excited molecule and reducing the intensity of the fluorescent light emitted. It is also known that the partial pressure of molecular oxygen may be measured via the fluorescence intensity of such an indicator substance. The fluorescent material may be supplied in a solvent. The partial pressure of the oxygen contained in this solvent will determine the degree of fluoresence intensity.

In a sensor element described in German Pat. No. 25 08 637, for instance, a thin film of the indicator solution is applied on a suitable transparent carrier material, and the fluorescent solution is covered by an oxygen-permeable membrane. On the carrier side of this set-up a lighting device and a photometer are located. The thin oxygen-permeable membrane will permit rapid equilibration of the partial oxygen pressure in the fluorescent layer and the adjoining medium outside the cover membrane. In the fluorescent layer diffusion will rapidly produce the partial oxygen pressure of the adjoining medium, and the intensity of the fluorescent light of the layer will vary accordingly. With this type of sensor element the partial oxygen pressure may be measured by optical means, even in aqueous media.

The noted German patent also proposes "leakproof" encapsulation of the indicator substance, i.e., the fluorescent material, in polymer foil. However, it does not describe any method of producing such sensor elements.

Before further discussing the problem of incorporating indicator molecules into polymers, a list will be given of the major aromatic hydrocarbons which may be used as indicators in a sensor element according to the invention. Among these most preferable are:

Carbazole, acridone, fluoranthene, 9,10-diphenylanthracene, chrysene, benz(a)anthracene, tetracene, pyrene, dibenz(ah)anthracene, perylene, benzo(ghi)perylene, coronene, anthanthrene, decacyclene, 1-aminoanthracene, 2-aminoanthracene, 1-aminopyrene.

In addition, many other fluorescent substances from the group of polycyclic, homocyclic or heterocyclic aromatic hydrocarbons will exhibit fluorescence upon the influence of molecular oxygen.

Indicator substances of the above type may be incorporated into a polymer by one of the following methods:

(1) Indicator substances should be chosen such that they are themselves soluble in a solvent for the selected polymer, and a common solution should be prepared of the indicator substance and the polymer. After evaporation of the common solvent, the polymer containing the indicator substance will remain.

(2) Apart from a common solvent, a polymer suspending agent may be used, provided that this agent is again suited as a solvent for the indicator substance.

(3) If polymerization of the employed polymer is taking place in a reaction mixture of several components, one of these components may be used as a solvent for the indicator substance at the same time.

This simple, conventional procedure entails a number of problems, making indicator molecules which are incorporated into polymers in this manner, unsuited for the purpose of the present invention. For example, evaporation of the common solvent will not lead to a molecular distribution of the indicator substance in the polymer, but will cause the indicator substance to crystallize out in the polymer. Although the crystallized indicator substance in the polymer will exhibit fluorescence, this fluorescence will not be influenced—at least not to a useful degree—by the presence of molecular oxygen.

Besides a fine distribution of microcrystals in the polymer, large aggregates of crystalline indicator substance were observed to build up in the polymer.

Even if there is a molecular distribution of the indicator substance in the polymer, which may be noted in certain cases, e.g., with polyvinylchloride solutions, the indicators incorporated in this manner will exhibit no fluorescence quenching due to molecular oxygen.

SUMMARY OF THE INVENTION

It is an object of the present invention to improve a sensor element and a method of the aforementioned kind such that the above disadvantages of the known devices will be eliminated, and such that an indicator substance may be incorporated in a polymer carrier in a simple manner to exhibit fluorescence or fluorescence quenching large enough to be used for measurement purposes.

According to the present invention this is achieved by the use of a cured silicone polymer as carrier material to which the indicator substance is added in solubilized form.

The suitability of a polymer carrier for the purpose of the present invention, for instance of a polymer membrane, is mainly determined by the oxygen permeability of the membrane material, which should be sufficiently high. Sensitivity is determined by the fluorescence decay time of the indicator substance used and by the oxygen permeability coefficient ($P_{O2}$) of the polymer material.

With the exception of silicones ($P_{O2} \approx 600.10^{-10} cm^2 s^{-1} cmHg^{-1}$), oxygen permeability coefficients are too low ($P_{O_2} < 35.10^{-10} cm^2 s^{-1} cmHg^{-1}$), and do not yield useful results with regard to oxygen sensitivity, even if the fluorescence decay times of the indicator substances used are large. The degree of oxygen quenching in the sensor element is determined by the fluorescence decay time of the indicator substance and by the oxygen permeability coefficient of the polymer material (fluorescence decay time being the average lifetime of excited state of a fluorescent molecule).

The use of a polymer of lesser oxygen permeability will imply the use of indicator molecules of large fluorescence decay times.

If a silicone polymer is used whose oxygen permeability is better than that of any other polymers, the use of indicator substances with relatively small fluorescence decay times ($\tau_o > 5$ ns) will already yield useful differences between fluorescence signals varying with the partial oxygen pressures.

But even if silicone polymers are used for carrying the indicator substances, the concentrations of these substances which may be incorporated by the usual methods described above will be too low to produce a fluorescence signal level high enough to be utilized for measurement purposes.

It has been surprisingly found, however, that the indicator substances lend themselves to chemical modification, i.e., they may be solubilized, so that sufficiently high concentrations of the indicator substances may be dissolved in the silicone material.

"Solubilization" means here that the solubility of a substance in a solvent (which may also be a polymer) is increased by modification of the substance (chemical modification).

Modification of the indicator substances is performed in analogy to the conventional Friedel-Crafts alkylation of aromatics.

It has thus been found that, in spite of an increased solubility of the fluorescent substance, the quenching behavior will essentially remain unaffected if the following steps are taken:

Dissolve the indicator substance and tertiary butyl chloride in a suitable solvent ($CS_2$), and react them, using aluminium chloride as a catalyst.

Extraction should be followed by washing and drying; removal of excess organic solvents by rotary evaporation will produce an oily residue which may be directly utilized as "solubilized indicator"; or: method as above, except that the indicator should be dissolved in an excessive amount of tertiary butyl chloride without addition of another solvent.

Subsequent to the above procedure, polymer or prepolymer mixtures with oxygen-sensitive indicator substances may be prepared which may then be processed into membranes, the indicator concentration in these mixtures being high enough to permit a useful signal yield even for thin films (e.g. of a film thickness smaller than $50\mu$). The polymer mixtures are processed into thin membranes by conventional techniques employing brushing, casting or other common polymer surface coating techniques. Another advantage of this type of procedure is that during polymerisation a thin membrane may be applied on a solid carrier material to produce a permanent bond.

Such thin polymer membrane containing indicator substances of the above type, which are bonded to a carrier material, have been employed to determine the oxygen content in gases by means of photometric measurement of fluorescence. As a special feature of this particular measurement technique, response times of down to 0.15 seconds may be achieved upon changeover from pure nitrogen to pure oxygen.

Although dissolving the indicator substance in the polymer carrier material will often suffice to prevent indicator losses to the environment, other methods of immobilizing the substance in the polymer carrier may be preferable for various applications:

Such methods include:
(a) Restriction of indicator mobility in the polymer by chemical modification of the indicator substance (alkylation with longer C chains).
(b) Covalent bonding of the indicator substance to the polymer material.

Like electrochemical sensors for measurement of gases, optical sensors must be calibrated with calibrating media of a known gas concentration. If a measurement of the partial oxygen pressure in liquids is required, and if it cannot be assumed that the calibrating medium has the same optical properties as the sample, the interface between membrane and sample can be expected to exhibit optical effects interfering with the fluorescence signal obtained. This is mainly due to the fact that the conditions of reflection at the interface between membrane and sample will depend on the optical properties of the sample medium, thus making the reflection of the excitation light and fluorescent light back into the sensor membrane dependent on the optical properties of the sample medium. This undesireable side effect may be avoided by providing the interface between membrane and sample medium with well-defined optical properties.

From German Pat. No. 25 08 637, for instance, it is known that the surface of the optical sensor of the measuring device may be metal-coated or blackened such that the influence of the optical properties of the sample medium is negligible.

In sensor elements according to the invention with a higher indicator concentration this has proved of disadvantage, since an adequately thin blackening or sealing coat may easily be removed from the surface of the sensor containing the indicator, while an increase in thickness in order to gain mechanical stability, would impair diffusion of oxygen from the sample area into the sensor interior.

For this reason in an embodiment of the present invention an additional layer of polymer of low transparency is applied on the side of the polymer carrier facing the sample, e.g., a silicone coating containing particles of ferrous oxide.

Another possibility of achieving optical independence of the sample medium is the incorporation of pigments, such as ferrous oxide particles, into the polymer membrane containing the indicator substance.

By the use of external fields of force during the cure time of the membrane these particles may be directed into a part of the indicator membrane close to the surface (examples of fields of force: gravitational, electric, magnetic fields).

According to a further embodiment of the invention, optical independence of the sample medium may also be established by incorporating during polymerization a thin mesh screen of metal or plastic on the side of the polymer carrier facing the sample. The meshes used in screen printing processes have been found suitable in this context.

DESCRIPTION OF A PREFERRED EMBODIMENT OF THIS INVENTION DEPICTED IN THE ENCLOSED DRAWING

By the above techniques a multi-layer sensor element may be prepared, as is shown in the enclosed drawing. A bottom layer 1 which is turned towards a lighting and photometric device (not shown here), and is irradiated by excitation light (hv), will serve as solid carrier (e.g. glass). A medium layer 2 is that layer of polymer containing the fluorescent indicator substance in molecular distribution such that a fluorescence signal (hv′) may be obtained depending on the oxygen content of the sample material adjacent to the sensor element. Above layer 2 there is an optical insulation layer 3 facing the sample material. Layers 2 and 3 are made of a polymer material with good oxygen permeability. The above two layers are homogeneously bonded by polymerization.

Carrier layer 1 could be dispensed with if no mechanical stability is required, or if the remaining two layers are held in a suitable frame. In this case the lighting device and photometer are located next to layer 2.

EXAMPLES (a) Dissolve 0.2 grams of solubilized (cf. page 6, paragraph 4) decacyclene in 10 grams of RTV-1 Silicone rubber (Elastosil E41, Wacker Chemie, West Germany); this solution should then be applied by means of a coating device on a degreased glass slide to a film thickness of approx. 20 μm. After curing of the silicone-/indicator layer, a homogeneously stirred mixture of 10 parts by weight of RTV-1 silicone rubber (Elastosil E43, Wacker Chemie, West Germany) and two parts by weight of ferrous oxide pigments should be applied by means of a coating device on the cured silicone/indicator layer to a film thickness of 20 μm. At the end of the curing cycle the sensor element will be ready for use.

(b) Prepare a silicone/indicator layer as under (a). After the silicone coating containing the indicator has been applied on the glass slide, the slide should be covered with a black mesh as used in screen printing (thread diameter =30 μm, open area =46 percent) by presssing it onto the silicone surface.

At the end of the curing cycle the sensor element will be ready for use.

We claim:

1. A sensor element which, when placed in contact with a sample containing oxygen, is capable of indicating the oxygen content in said sample, said sensor element comprising a cured silicone polymer carrier matrix which is permeable to oxygen molecules and a chemically modified, solubilized, oxygen-sensitive fluorescent indicator substance which is generally homogeneously embedded within said cured silicone polymer carrier matrix, said oxygen-sensitive fluorescent indicator substance, upon excitation, emitting light of a certain wavelength and of varying intensity depending on the amount of oxygen from said sample in contact therewith, said sensor element being produced by a method which comprises the steps of (a) combining an oxygen-sensitive fluorescent indicator substance with tertiary butyl chloride,
 (b) catalytically reacting said oxygen-sensitive fluorescent indicator substance and said tertiary butyl chloride and recovering a solubilized fluorescent indicator substance,
 (c) mixing said solubilized fluorescent indicator substance with an uncured silicone polymer to form a homogeneous mixture, and
 (d) curing said mixture to form said sensor element.

2. A sensor element according to claim 1, wherein said cured silicone polymer carrier matrix is shaped to include a flat surface which is intended to face the sample containing oxygen, and wherein said sensor element includes a polymer layer having low transparency covering said flat surface of said cured silicone polymer carrier, said polymer layer being permeable to oxygen molecules.

3. A sensor element according to claim 2, wherein said polymer layer comprises a silicone coating having particles of ferrous oxide therein.

4. A sensor element according to claim 1, wherein said cured silicone polymer carrier matrix is shaped to include a flat surface which is intended to face the sample containing oxygen, and wherein said cured silicone polymer carrier matrix includes a thin mesh screen embedded therein adjacent said flat surface thereof.

5. A sensor element according to claim 1, wherein said fluorescent indicator substance is a compound which includes molecules selected from the group consisting of polycyclic aromatic molecules, homocyclic aromatic molecules and heterocyclic aromatic molecules.

6. A sensor element according to claim 5, wherein said fluorescent indicator substance comprises a polycyclic aromatic hydrocarbon which displays fluorescence decay times $\tau_o$ greater than 5 ns.

7. A sensor element according to claim 1, wherein said cured silicone polymer carrier matrix includes pigment particles therein.

8. A sensor element according to claim 7, wherein said pigment particles are ferrous oxide particles.

9. A sensor element according to claim 7, wherein said cured silicone polymer carrier matrix is generally plate shaped so as to have a first flat surface which is intended to face the sample containing oxygen and a second flat surface which is intended to face away from the sample containing oxygen, and wherein said pigment particles are contained in said cured silicone polymer carrier matrix in increasing amounts in the direction between said second flat surface and said first flat surface.

10. A sensor element according to claim 1, wherein said fluorescent indicator substance includes hydrocarbon chains containing between 3 and 20 carbons atoms.

11. A method of producing a sensor element which, when placed in contact with a sample containing oxygen, is capable of indicating the oxygen content in said sample, said sensor element comprising a cured silicone polymer carrier matrix which is permeable to oxygen molecules and a chemically modified, solubilized, oxygen-sensitive fluorescent indicator substance which is generally homogeneously embedded within said cured silicone polymer carrier matrix, said oxygen-sensitive fluorescent indicator substance, upon excitation, emitting light of a certain wavelength and of varying intensity depending on the amount of oxygen from said sample in contact therewith, said method comprising the steps of (a) combining an oxygen-sensitive fluorescent indicator substance with tertiary butyl chloride,
 (b) catalytically reacting said oxygen-sensitive fluorescent indicator substance and said tertiary butyl chloride and recovering a solubilized fluorescent indicator substance, (c) mixing said solubilized fluorescent indicator substance with an uncured silicone polymer to form a homogeneous mixture, and (d) curing said mixture to form said sensor element.

12. A method according to claim 11, wherein in step (a) said oxygen-sensitive fluorescent indicator substance and said tertiary butyl chloride are dissolved in a solvent.

13. A method according to claim 12, wherein said solvent consists of $CS_2$.

14. A method according to claim 11, wherein in step (b) said oxygen-sensitive fluorescent indicator substance and said tertiary butyl chloride are reacted in the presence of aluminum chloride.

15. A method according to claim 11, wherein in step (a) said oxygen-sensitive fluorescent indicator substance is dissolved in an excess of tertiary butyl chloride.

16. A method according to claim 11, including between steps (c) and (d) the step (c') of moulding said mixture.

17. A method according to claim 16, wherein in step (c') said mixture is moulded into the general form of a flat plate.

18. A method according to claim 16, including between steps (c) and (c') the step (c'') of adding ferrous oxide particles to said mixture, and between steps (c'') and (c') the step (c''') of applying a force field to said moulded mixture so as to cause said ferrous oxide particles to be graded in amount through said moulded mixture.

* * * * *